United States Patent
Hörmann et al.

(10) Patent No.: US 10,850,900 B2
(45) Date of Patent: Dec. 1, 2020

(54) PROCESS FOR INDIVIDUALLY MARKING A MEDICAL PRODUCT PRESENT UNDER FILM OR IN A BAG AND MARKED PRODUCT

(71) Applicant: Fresenius Medical Care Deutschland GmbH, Bad Homburg (DE)

(72) Inventors: Jörn Hörmann, Heusweiler (DE); Sebastian Meisinger, Marpingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 98 days.

(21) Appl. No.: 15/513,773

(22) PCT Filed: Sep. 25, 2015

(86) PCT No.: PCT/EP2015/072152
§ 371 (c)(1),
(2) Date: Mar. 23, 2017

(87) PCT Pub. No.: WO2016/046388
PCT Pub. Date: Mar. 31, 2016

(65) Prior Publication Data
US 2017/0291745 A1 Oct. 12, 2017

(30) Foreign Application Priority Data

Sep. 26, 2014 (DE) .................. 10 2014 113 959

(51) Int. Cl.
*B65D 65/02* (2006.01)
*A61J 1/10* (2006.01)
(Continued)

(52) U.S. Cl.
CPC ................ *B65D 65/02* (2013.01); *A61J 1/10* (2013.01); *A61M 1/167* (2014.02); *B29C 65/02* (2013.01);
(Continued)

(58) Field of Classification Search
CPC ........... B65D 65/02; A61M 1/167; A61J 1/10; B29C 65/02; B29C 65/18; B29C 65/60; B29C 66/472; B29C 66/8491
(Continued)

(56) References Cited

U.S. PATENT DOCUMENTS 2,899,347 A * 8/1959 Kindseth ................. B29C 66/43
156/209
3,348,759 A * 10/1967 Johnson ............... B65D 33/004
383/40
(Continued)

FOREIGN PATENT DOCUMENTS

| CN | 2880072 | 3/2007 |
|----|---------|--------|
| CN | 103221195 | 7/2013 |

(Continued)

OTHER PUBLICATIONS

International Search Report in International Application No. PCT/EP2015/072152, dated Dec. 11, 2015, 7 pages (with English translation).
(Continued)

*Primary Examiner* — Chun Hoi Cheung
(74) *Attorney, Agent, or Firm* — Fish & Richardson P.C.

(57) ABSTRACT

A process for the marking of a film or a bag, which consists of a film at least in sections, wherein the film or the bag comprises a medical product or is provisioned or prepared for the uptake of such, wherein the process comprises connecting a film strip with, in, to and/or on the film, wherein the film strip carries information for marking the medical product.

15 Claims, 2 Drawing Sheets

(51) Int. Cl.
*A61M 1/16* (2006.01)
*B29C 65/02* (2006.01)
*B29C 65/48* (2006.01)
*B29C 65/60* (2006.01)
*B29C 65/00* (2006.01)
*B29L 31/00* (2006.01)

(52) U.S. Cl.
CPC .............. *B29C 65/48* (2013.01); *B29C 65/60* (2013.01); *B29C 66/472* (2013.01); *B29C 66/8491* (2013.01); *A61J 2205/30* (2013.01); *A61M 2205/6072* (2013.01); *B29L 2031/712* (2013.01)

(58) Field of Classification Search
USPC .... 206/438, 461–471; 283/18, 101, 106, 81; 604/403, 408–414; 383/22–24, 78–79, 383/84, 80; 248/691, 205.3
See application file for complete search history.

(56) References Cited

U.S. PATENT DOCUMENTS

| | | | | |
|---|---|---|---|---|
| 3,503,265 A | * | 3/1970 | Isreeli | A61B 5/117 73/864.24 |
| 3,963,174 A | * | 6/1976 | de Lyra | B65D 27/28 229/80 |
| 4,083,451 A | * | 4/1978 | Hair | B29C 65/02 206/461 |
| 4,526,404 A | * | 7/1985 | Vazquez | A61G 12/00 206/232 |
| 4,846,005 A | * | 7/1989 | Bacehowski | A61J 1/10 73/864.81 |
| 5,172,980 A | | 12/1992 | Provost | |
| 5,314,421 A | * | 5/1994 | Leuenberger | G09F 3/02 283/117 |
| 5,507,525 A | * | 4/1996 | Leuenberger | G09F 3/02 283/117 |
| 6,082,777 A | * | 7/2000 | Grosskopf | B32B 7/04 283/81 |
| 6,202,260 B1 | | 3/2001 | Clune et al. | |
| 6,205,623 B1 | | 3/2001 | Shephard et al. | |
| 6,235,369 B1 | | 5/2001 | Shepard et al. | |
| 6,851,161 B2 | | 2/2005 | Kingsford et al. | |
| 7,155,854 B2 | * | 1/2007 | Dickinson | B32B 7/06 40/775 |
| 7,163,706 B2 | | 1/2007 | Shepard et al. | |
| 7,186,025 B2 | | 3/2007 | Shepard et al. | |
| 7,308,783 B2 | | 12/2007 | Shepard et al. | |
| 7,395,583 B2 | | 7/2008 | Clune et al. | |
| 7,703,687 B2 | | 4/2010 | Barczyk et al. | |
| 8,051,540 B2 | | 11/2011 | Gallant et al. | |
| 8,151,988 B2 | * | 4/2012 | Smith | B65D 75/366 206/461 |
| 8,579,878 B2 | * | 11/2013 | Seidl | G09F 3/10 283/101 |
| 8,858,077 B2 | | 10/2014 | Shepard | |
| 2002/0056989 A1 | * | 5/2002 | Lewis-Leander | G09F 3/0288 283/81 |
| 2003/0072676 A1 | | 4/2003 | Fletcher-Haynes | |
| 2004/0172007 A1 | | 9/2004 | Grimm | |
| 2008/0275421 A1 | * | 11/2008 | Tanaka | A61J 1/10 604/404 |
| 2009/0131903 A1 | * | 5/2009 | Shoji | A61J 1/16 604/410 |
| 2012/0283688 A1 | * | 11/2012 | Seidl | G09F 3/10 604/408 |
| 2014/0154442 A1 | * | 6/2014 | Bent | A61J 1/10 428/35.2 |

FOREIGN PATENT DOCUMENTS

| | | |
|---|---|---|
| DE | 1673107 | 5/1970 |
| DE | 1946761 | 3/1971 |
| DE | 69305474 | 5/1997 |
| DE | 10-2011-100156 | 11/2012 |
| EP | 1127011 | 8/2001 |
| EP | 2509057 | 10/2012 |
| GB | 2490306 | 10/2012 |
| JP | H6-296659 | 10/1994 |
| JP | 2000006989 | 1/2000 |
| WO | 2016046388 | 3/2016 |

OTHER PUBLICATIONS

International Preliminary Report on Patentability in International Application No. PCT/EP2015/072152, dated Mar. 28, 2017, 15 pages (with English translation).

* cited by examiner

PROCESS FOR INDIVIDUALLY MARKING A MEDICAL PRODUCT PRESENT UNDER FILM OR IN A BAG AND MARKED PRODUCT

CROSS-REFERENCE TO RELATED APPLICATIONS

This application is the national stage entry of International Patent Application No. PCT/EP2015/072152, filed on Sep. 25, 2015, which claims priority to German Patent Application No. 10 2014 113 959.3, filed on Sep. 26, 2014, the entire contents of which are hereby incorporated by reference.

TECHNICAL FIELD

The present disclosure concerns a process for marking a medical product in or under a film or in a bag. In addition, it concerns a marked medical product.

BACKGROUND

Medical products, such as medical solutions or dialysis fluids, which are often packaged in film or bags, are marked, in particular according to legal requirements, for example in order to prevent non-intended use and/or counterfeiting of products.

SUMMARY

Aspects of this disclosure relate to providing a further process for marking a medical product present in or under film or in a bag, as well as a medical product, which is suitably marked in a film or in a bag.

Aspects of this disclosure relate to a process for marking a film or a bag with a medical product or for the reception of a medical product. The medical product can be, for example, a medical device or a medical consumable material.

The film or the bag is intended to receive, cover or otherwise package the medical product, or does just that.

The process comprises the connecting (for example welding or other joining) of a film strip with, in, on or on top of at least one section of the film or the bag, preferably with an outside or surface of the latter or with itself, preferably in such way that a positive connection results.

The film strip carries information, particularly such that can be captured optically, for marking the medical product or exhibits such information.

The medical product according to some embodiments is present inside or under a film or in a bag. In this, at least one film strip is connected with the film or the bag or with itself. The film strip carries information for marking the medical product.

Embodiments can possess some, a few or all of the following features in any combination, as long as this is not technically impossible as recognised by the person skilled in the art. In all of the following embodiments, the use of the expression "can be" and "can have", etc., is to be understood to be synonymous to "is preferably" and "has preferably", respectively and is intended to illustrate embodiments.

Whenever numbers are mentioned herein, they will be recognised as the statement of a lower limit by the person skilled in the art. As long as this does not lead to a contradiction as recognised by the person skilled in the art, the person skilled in the art will, for example, at the disclosure of "one", always read "at least one" as well. The present invention comprises this comprehension as well as the interpretation that a number such as "one" can alternatively mean "exactly one", wherever this is not technically impossible as recognised by the person skilled in the art.

Both is comprised by the present invention and is valid for all numbers used herein.

For increased readability, a film is mainly mentioned in the following. This can be part of a bag, for example its outer layer. Wherever a film is mentioned in the following, this is also valid for a bag, as long as this is not recognisably impossible for the person skilled in the art.

In certain exemplary embodiments, the connecting is welding, gluing, punch riveting, or any combination thereof.

In specific exemplary embodiments, the joining process used is chosen from a group of joining processes, which comprises or consists of welding, gluing, punch riveting or any combination thereof.

In some exemplary embodiments, the medical consumable material is a medicine or a solution used in dialysis.

In certain exemplary embodiments, the medical product is a blood cassette, a blood tube set, a part thereof or the like.

In some exemplary embodiments, the bag is a solution bag, thus a bag or a bag shell, which is filled with solution. The solution can be intended, for example, for dialysis.

The film strip can possess any suitable form. It can be designed as a strip, a plane, a section or the like.

In some exemplary embodiments, the film strip is or is being connected, for example welded or glued, exclusively to film material of the film.

In some exemplary embodiments of the process, the film strip is not or is not being connected to the film, but exclusively with itself. Thus, a first section of the film strip is connected with a second section of the film strip.

In certain exemplary embodiments of the process, the film possesses in at least one section thereof a two-layered design. In this, at least a first film layer is or is being connected onto or with a second film layer, for example welded. At least one section of the film strip is or is being arranged between the first film layer and the second film layer and is being connected, for example welded or glued, with at least the first film layer and/or the second film layer, for example with the inner surfaces thereof.

In some exemplary embodiments, the film strip is or is being connected, for example welded or glued, to at least one outer layer or outer surface of the film or of the first film layer.

In some exemplary embodiments, the process comprises the generating of a passage opening, for example of a punching gap, in one section of the film or bag, which is present in a single layer or as multiple layers or the providing of a film or of a bag with such a passage opening. Furthermore, it comprises the arranging of the film strip on both sides of the passage opening or the application of the film strip along the film on both sides of the passage opening as well as the connecting, for example welding or gluing or punch riveting, of the film strip with itself through the passage opening.

In certain exemplary embodiments of the product, the film is in at least one section thereof at least two-layered. In this, at least one first film layer rests at least by section on at least a second film layer and is connected therewith at least by section, for example via glue connection, welded connection or a welding seam. In this embodiment according to the invention, at least one section of the film strip is arranged between the first film layer and the second film layer. At least one section of the film strip is connected to at least one section of the first film layer and/or at least one section of the second film layer.

In a few exemplary embodiments, the film strip is not connected to the film, but only to itself.

In some exemplary embodiments of the product, the film or the bag possesses in at least one section, in which it is present in a single layer or multiple layers, a passage opening. In this, the film strip is present on both sides of the passage opening and is connected to itself via the passage opening.

"Single layer" can mean in certain embodiments a film layer, wherein the film layer possesses exactly one inner side and exactly one outer side, wherein the inner side can be in contact with the medicinal product and the outer side can be in contact with the surroundings or the atmosphere.

In certain exemplary embodiments "two-layered" can mean two film layers, wherein each of the two film layers can possess exactly one inner side and exactly one outer side, wherein each inner side can be in contact with the medicinal product and each outer side can be in contact with the surroundings or atmosphere.

The marking can be performed in any way. Preferably and solely by example, the marking can be performed in one of the following ways: by inkjet, laser, thermal transfer or hot embossing process.

Codes can be, for example, bar codes, 2D codes, data matrix codes or others.

The bag films are transparent in certain embodiments. In these embodiments, only the film strip is designed in colour or in black. This coloured or black design carries the advantage of an increased readability through increase of the contrast between background and inscription (for example a black code on a white background), such that a better automatic reading in is ensured as well.

Some or all of the embodiments can possess one, several or all of the advantages mentioned above and/or below.

One possible advantage of the process for marking a film or a bag with information on the medicinal product contained therein, can be that marking in the form of codes, plain text or symbols enables a production of variable data and thus a better transparency regarding errors and complaints within a serialisation of products as single products can be traced instead of batches. Also, advantageously, a detailed process tracking, for example in connection with production reports, is possible.

With the aid of the process, advantageously, such film materials can for the first time be used as film strips, which possess especially suitable surface properties for a good colour adhesion and/or a good colour representation for the marking, without having to use these films as film for the complete encasement of the medicinal product.

The film strip with the marking can preferably be connected to the film in such a way that the film strip can only be destructively removed or separated from the film of the bag, preferably at least in use or in the usual handling in the application environment, i.e., outside the laboratory or the like. This is of advantage as the labelling or marking of the medical product is firmly connected to the medical product or its film or bag, respectively and should remain this way.

Furthermore, advantageously, the colour of the film of the bag for the medicinal product can be chosen independently of the colour of the marking. For example, the film could be white and the marking or single components of the marking could, with the suitable choice of a further colour (except for white) for the background, could also be white.

Because of the separate implementation of the film on the one hand and of the film section with the marking on the other hand, the marking can, advantageously, be read out and detected with ease. A required contrast can be chosen freely. This is particularly advantageous if a certain class or quality of the marking is required for example in the approval of medicinal products, as for example a certain or sufficient contrast (for example a black/white contrast).

Furthermore, advantageously, it can be achieved that in a labelling or marking with a laser process (for example in a laser colour transfer marking), the film of the bag remains intact and its barrier property is not impaired, even if the laser parameters or laser effect are subject to variation.

The application of a film section with the marking, independently of place and time of production and possibly filling of, for example, a bag with a medical product and the connecting of film section with film, enables furthermore advantageously that the printing on a film section can be carried out independently of a timing of a production line for the production of the filled bags. The merging of the printed film section with the filled bag is only carried out by the joining process or connecting process, for example, by the welding process.

A direct connection of a printed film section with the surface of a film of a bag can be prevented, advantageously, in certain embodiments, by connecting the printed film section with the film via an internal connection (see FIG. 2), for example by gluing, welding or the like. Thereby, advantageously, surfaces, outer surfaces or outer layers can be used for the film, which are on one hand connectable only poorly or not at all, on the other hand, however, show good material properties elsewhere (for example, high barrier properties, such as $SiO_x$ film coatings).

Furthermore, the process enables, in certain embodiments, to choose and use materials for the printable film section, which are not connectable or weldable with the film for the bag, but only with themselves. Thus, advantageously, the material for the film section and the film of the bag can be chosen independently of each other.

By using the process it could finally be possible, advantageously, to apply the falsified medicines directive 2011/62/EU to medical products in bags through a bag specific individual labelling requirement (serialisation). Furthermore, the process makes it possible to generate variable data for the execution of the labelling in a first step and to firmly connect this data as individual label with the bag containing the medical product.

All advantages achievable through the process can be achieved, without limitations, in certain embodiments of the product.

BRIEF DESCRIPTION OF THE FIGURES

In the following, embodiments are described with reference to the enclosed figures in a purely exemplary fashion.

DETAILED DESCRIPTION

The following figures describe an example, in which a film strip is welded to a film. This example is just that, purely exemplary. Other connecting processes or joining processes, which contain no welding or do not exclusively contain welding, are also contemplated, however, are not illustrated with figures in order to avoid repetition.

Figure 1:
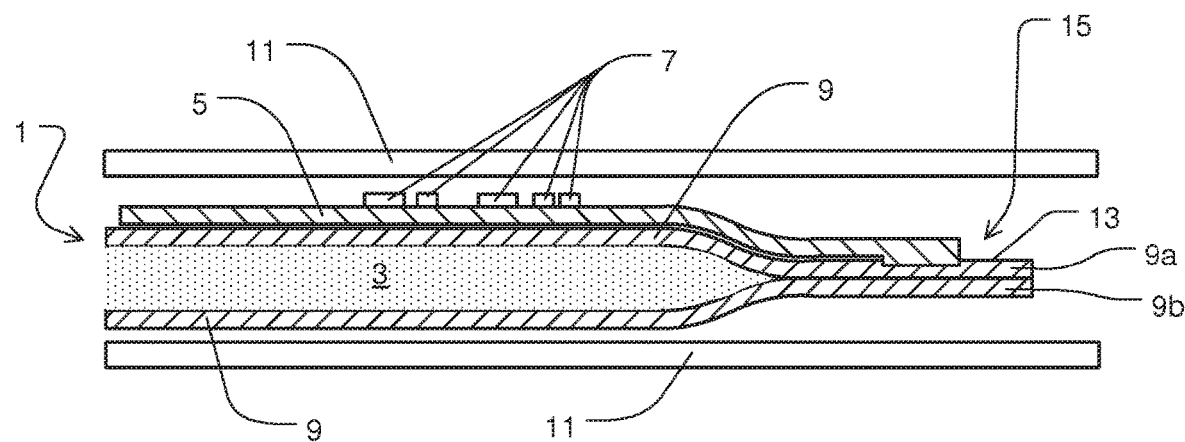
FIG. 1 is a simplified sectional view a medical product in a (film) bag with a film, which bag possesses a film strip with information for the marking of the medical product, in a first embodiment.

FIG. 1 shows a section of a bag 1 in a simplified sectional view, wherein the bag encloses a medicinal product 3 (here, a medical consumable material such as a dialysis fluid or dialysis solution) as well as a film strip 5 with information for the marking 7 of the medical product 3. The bag 1 is produced from a film 9, is equivalent to such or at least possesses a film 9.

Exemplarily, the bag 1 is surrounded, packaged or protected by an outer film 11, which can, accordingly, be described as a surrounding film, protective film or packaging. The outer film 11 is only shown schematically in the figures. It is optional and, if present, preferably arranged to surround the bag 1 entirely.

The marking 7 can be applied to the film strip 5 in different ways. For example, the film strip 5 can be printed on with an ink. Additionally or alternatively, the film strip 5 can be marked using a laser process or gluing.

In the purely exemplary first embodiment of FIG. 1, the film strip 5 is connected with an outer surface 13 (or an outer layer or a first film layer 9a if the film 9 is arranged in multiple layers as in the example of FIG. 1) of the film 9 via at least one welded connection or welding point 15. To this end, the material of the film strip 5 and the material of the film 9 are chosen to be weldable to each other. In other exemplary embodiments according to the invention, in which the film strip 5 is not connected with the film 9 via a welded connection, but instead, for example via a glue connection, the welded connection or welding point 15 is thus a glue connection or a gluing point, etc.

For this purpose, thermoplastics are a particularly suitable film material and film strip material, as these typically soften, become plastically malleably free-flowing and are weldable under the influence of heat. Thermoplastics such as polypropylene (PP) or polyethylene (PE), which are connectable, for example weldable, using the usual joining processes, in particular the joining processes mentioned herein, as well as polyethylene terephthalate (PET) could be used.

The area of the welded connection 15 can, for example, be strip shaped, seam shaped or flap shaped (the longitudinal arrangement of the strip/the seam or the flap runs perpendicular to the plane of the drawing in FIG. 1).

In the end of the bag 1 shown in FIG. 1 on the right, the film 9 in a first film layer 9a abuts upon a second film layer 9b and in this position is welded to the former at least in sections. This welding is not shown in FIG. 1 and is independent of the welding point 15, in which the film strip 5 is connected to the film 9 by welding.

The welding 15 is carried out in the example of FIG. 1 particularly at the outer edge of the bag 1 or in the area, in which the first film layer 9a overlaps with the second film layer 9b and where they are welded together. The area, in which the first film layer 9a and the second film layer 9b are welded together, can be arranged further inward in relation to the welding 15 (directed toward the bag contents or the medical product 3), can overlap in the area of the welding 15 of the film strip 5 with the film 9 or can be arranged further outward (in FIG. 1 to the right).

Figure 2:
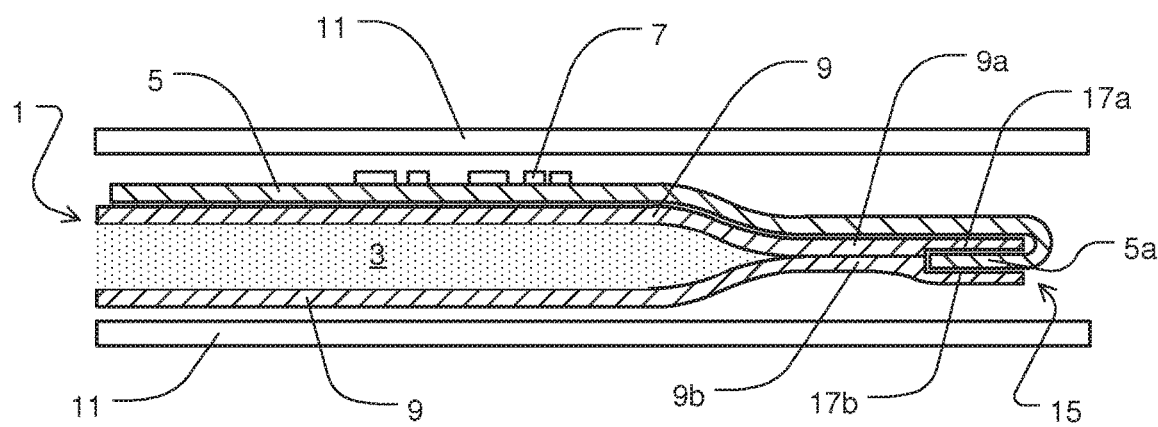
FIG. 2 shows the bag from FIG. 1 with a film strip with information for the marking of the medical product, in a second embodiment.

FIG. 2 shows the bag 1 of FIG. 1, the film strip 5, which carries information for the marking 7 of the medical product 3, however, is attached to the film 9 in a different way from the one in FIG. 1.

As opposed to the first embodiment of FIG. 1, in the second embodiment in FIG. 2, the film strip 5 is arranged in at least a section 5a between a section of the first film layer 9a and a section of the second film layer 9b.

In the example of FIG. 2, the film strip 5 is welded to two interior surfaces of the film 9 or with each of the internal face 17a of the first film layer 9a and the internal face 17b of the second film layer 9b. In particular, the film strip 9 is welded in the welding area 15 bilaterally, that is with both its outer surfaces (in FIG. 2 thus with the upper and lower surface), with the two internal faces 17a of the first film layer 9a facing each other in the example of FIG. 2 or the internal face 17b of the second film layer 9b of the film 9, respectively. In other embodiments according to the invention, the film strip is welded to only one of the internal faces 17a, 17b with its section 5a.

Figure 3:
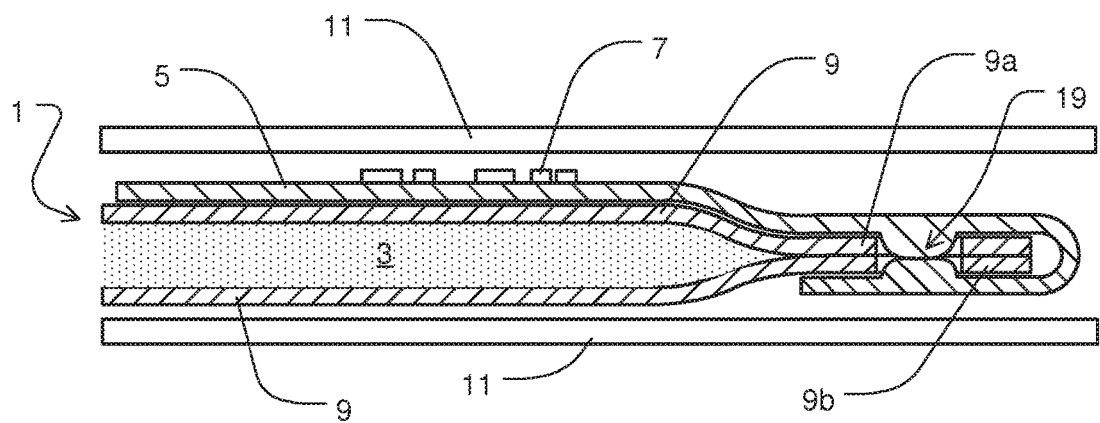
FIG. 3 shows the bag from FIG. 1 with a film strip with information for the marking of the medical product, in a third embodiment.

FIG. 3 shows the bag from FIG. 1 with a medical product 3 as well as a further arrangement and mounting of the film strip 5 on the film 9 or the bag, respectively.

As opposed to FIG. 1 as well as FIG. 2, in FIG. 3, the film strip 5 is not welded to the film 9 of the bag 1, but with itself in at least one welding 19. Specifically, in the welding 19, a section of the film strip 5 is welded with a further section of the film strip 5, preferably exclusively with itself. To this end, ideally, the material of the film strip 5 is weldable to itself. Alternatively, the film strip 5 could be suitably coated or show a different or modified material, at least in the area of the welding 19 of the film strip with itself, in order to ensure the weldability of the film strip or its coating, respectably, with itself.

Figure 6:
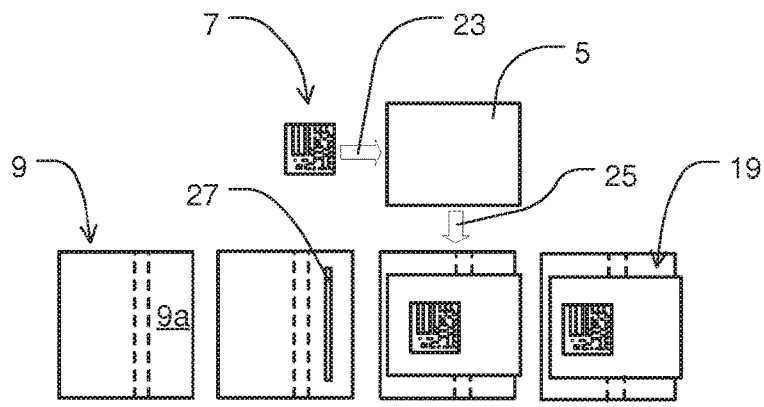

The welding of the film strip 5 with itself is possible in the example of FIG. 3 as the bag 1 possesses a passage opening in its (in FIG. 3) right side end portion, in which the first film layer 9a and the second film layer 9b are connected to each other, wherein the passage opening passes through top surface as well as bottom surface of the bag 1. The passage opening can be a continuous slot 27 as shown in FIG. 6 as it is explained in the section concerning FIG. 6. Other shapes than a slot shape, for example round, rectangular or the like, are possible for the passage opening as well.

On account of the passage opening, the welding of the film strip with itself can be carried out through the film 9. The welding of the film strip 5 through the passage opening connects the film strip 5 positively in relation to the film 9 or the bag 1, not requiring a non-positive or materially bonded connection therewith. Advantageously, this allows choosing materials for the film 9 on the one hand and for the film strip 5 on the other hand, which are not weldable to each other or, possibly, are only weldable to each other when a special effort is made.

Figures 4, 5:
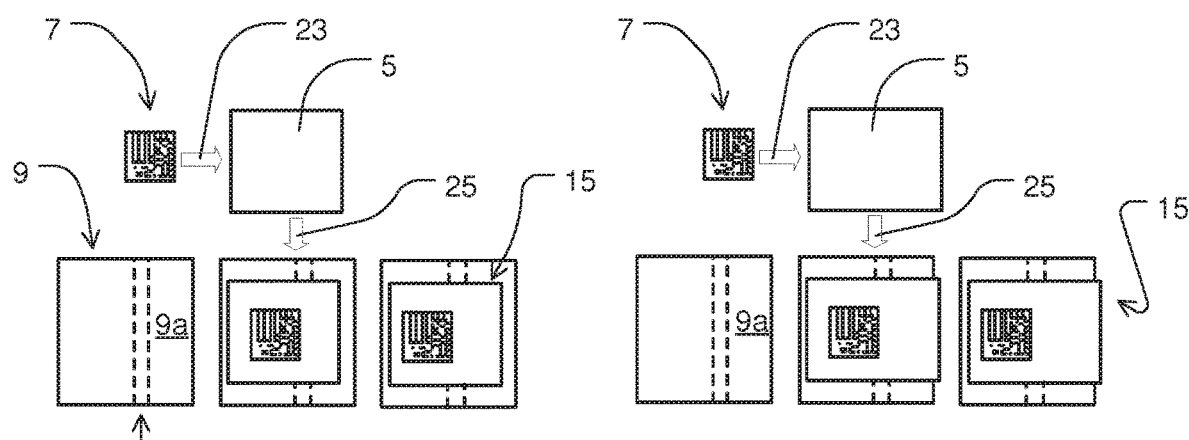
FIGS. 4 to 6 each show steps for the application of the marking on the film strip as well as the subsequent connection of the film strip with the bag.

FIG. 4 shows possible steps, and in certain embodiments even all steps, which are required for applying the marking 7 on the film strip 5 as well as for the subsequent connecting of the film strip 5 with the film 9 of the bag 1 according to the embodiment of FIG. 1.

The area of a welding or welding seam 21 of the overlapping first and second film layers 9a, 9b of the film 9 (the welding of the film layers 9a, 9b for sealing the bag 1) is shown in dashes as stripes.

The area of the welding 15 of the film strip 5 with the film 9 or of the first film layer 9a lies particularly in the outer area (in FIG. 4 in the right side end portion of the film 9).

Initially, in a first step 23, the marking 7 is applied to the film strip 5. This can be carried out by printing on the film strip 5 with ink or with the aid of a laser labelling process. Subsequently, in a second step 25, the film strip 5, which was printed upon or which was marked in a different way, is welded to the film 9. Preferably, the film strip 5 does not cover the entire width of the film 9.

It is noted that, according to the invention, the steps 23 and 25 could be carried out in opposite order from the one described herein. This is also true for the embodiments, which are described in connection with FIGS. 5 and 6.

FIG. 5 shows, in analogy to FIG. 4, possible steps, and optionally all steps, for applying the marking 7 on the film strip 5 as well as for the subsequent welding of the film strip 5 with the film 9 of the bag 1 according to the embodiment of FIG. 2.

In the area of the welding 15 of the film strip 5, the film strip 5 is connected via its section 5a with the internal surfaces 17 (see FIG. 2) of the film 9, which cannot be seen in FIG. 5.

Contrary to FIG. 4, the film strip 5 thus protrudes beyond the right margin of the film 9, at least beyond the margin of one film layer (here, the first film layer 9a).

FIG. 6 shows, in analogy to FIG. 4, possible steps, optionally even all steps, for applying the marking 7 on the film strip 5 as well as for the subsequent connecting of the film strip 5 with the film 9 of the bag 1 according to the embodiment of FIG. 3.

Contrary to FIG. 4 and FIG. 5, preferably, the film strip 5 in FIG. 6 is preferably not materially bonded and optionally also not non-positively connected, particularly not welded, to the film 9. Furthermore, one section of the film strip 5 is welded to another section of the film strip 5 and thus to itself.

For bringing together the two sections of the film strip 5 to be welded together, the film 9 possesses, for example, a passage opening, preferably a continuous slot 27, as this is easy to produce.

The passage opening, herein the slot 27, preferably has a length, which is at least as large as the width of the film strip 5. In this way, the film strip 5 can be passed through the passage opening without force and without warping, which could impede its welding.

In the right side drawing of FIG. 6, this continuous slot 27 is covered in the area of the welding by the film strip 5 carrying the marking 7 and is not visible.

The film strip 5 can be integrally formed. It can also be produced in two or several parts. If it is produced in several parts, then a first section thereof is placed on the upper face of the film 9, thus on the first film layer 9a, a second section thereof is placed on the lower face of the film 9, thus on the second film layer 9b. A welding is carried out through the passage opening as presently described. If both sections are large enough, then the film strip 5 as a whole forms a positive connection inside the passage opening or the film 9, respectively.

LIST OF REFERENCE NUMBERS 1 bag
3 medical product
5 film strip
5a section of the film strip
7 marking; information for marking
9 film
9a first film layer
9b second film layer
11 outer film
13 outer surface, outer layer of the film
15 welding of the film strip with the film
17a internal face, internal layer of the first film layer 9a
17b internal face, internal layer of the second film layer 9b
19 welding of the film strip with itself
21 welding seam or welding of the films for sealing of the bag
23 step for applying a marking on the film strip
25 step for applying the marked film strip on the film
27 continuous slot

The invention claimed is:

1. A process for marking a film or a bag which possesses the film at least in sections, wherein the film or the bag possesses or surrounds a medical product or is configured to possess or surround a medical product, the process comprising:
producing a passage opening through one section of the film, the passage opening comprising a continuous slot and having a first side and a second side;
arranging a film strip relative to the film such that a first portion of the film strip is on the first side of the passage opening and a second portion of the film strip is on the second side of the passage opening, wherein the film strip carries information for marking the medical product; and
securing the film strip to the film by creating a weld between the first and second portions of the film strip such that the weld is within the continuous slot,
wherein the continuous slot has a length that is at least as large as a width of the film strip.

2. The process of claim 1, wherein the film is part of the bag.

3. The process of claim 1, wherein the bag contains the medical product.

4. The process of claim 1, wherein the information comprises at least one of a code, plain text, or a symbol.

5. The process of claim 1, wherein the film comprises a first material and the film strip comprises a second material different from the first material.

6. The process of claim 5, wherein the second material comprises surface properties configured to allow color adhesion of the information.

7. The process of claim 1, wherein securing the film strip, via the weld, to the film comprises forming an irreversible connection such that removing the film strip from the film comprises destruction of at least one of the film strip or the film.

8. A medical product present inside or under a film, wherein a film strip is secured to the film, wherein the film strip carries information for marking of the medical product, wherein a first portion of the film strip is connected to a second portion of the film strip via a weld connection, wherein at least one section of the film is formed in at least two layers, wherein the at least one section of the film defines a passage opening comprising a continuous slot through one or more of the at least two layers, wherein the film strip is present on both sides of the passage opening, and wherein the weld connection of the film strip to itself is in the continuous slot, and wherein the continuous slot has a length that is at least as large as a width of the film strip.

9. The medical product according to claim 1, wherein the film strip is connected to at least one outer layer or outer face of the film.

10. The medical product of claim 8, wherein the film is part of a bag.

11. The medical product of claim 10, wherein the bag contains the medical product.

12. The medical product of claim 8, wherein the information comprises at least one of a code, plain text, or a symbol.

13. The medical product of claim 8, wherein the film comprises a first material and the film strip comprises a second material different from the first material.

14. The medical product of claim 13, wherein the second material comprises surface properties configured to allow color adhesion of the information.

15. The medical product of claim 8, wherein the film strip is secured to the film such that removing the film strip from the film comprises destruction of at least one of the film strip or the film.

* * * * *

UNITED STATES PATENT AND TRADEMARK OFFICE
CERTIFICATE OF CORRECTION

| | | |
|---|---|---|
| PATENT NO. | : 10,850,900 B2 | Page 1 of 1 |
| APPLICATION NO. | : 15/513773 | |
| DATED | : December 1, 2020 | |
| INVENTOR(S) | : Jörn Hörmann and Sebastian Meisinger | |

It is certified that error appears in the above-identified patent and that said Letters Patent is hereby corrected as shown below:

On the Title Page

Column 1 (Inventors), Line 1, delete "Heusweiler" and insert --St. Ingbert--.

In the Claims

Claim 9, Column 8, Line 65, delete "claim 1," and insert --claim 8,--.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*